(12) United States Patent
Culp et al.

(10) Patent No.: US 6,945,937 B2
(45) Date of Patent: Sep. 20, 2005

(54) ULTRASOUND APPARATUS AND METHOD FOR AUGMENTED CLOT LYSIS

(75) Inventors: William C. Culp, Little Rock, AR (US); James D. Wilson, Benton, AR (US)

(73) Assignee: Board of Trustees University of Arkansas, Little Rock, AR (US)

( * ) Notice: Subject to any disclaimer, the term of this patent is extended or adjusted under 35 U.S.C. 154(b) by 0 days.

(21) Appl. No.: 10/934,916

(22) Filed: Sep. 3, 2004

(65) Prior Publication Data

US 2005/0085748 A1 Apr. 21, 2005

Related U.S. Application Data

(60) Provisional application No. 60/501,000, filed on Sep. 8, 2003.

(51) Int. Cl.[7] ............................................. A61B 8/00
(52) U.S. Cl. ...................................................... 600/437
(58) Field of Search ................................ 600/437–472; 424/9.51–9.52

(56) References Cited

U.S. PATENT DOCUMENTS

| | | |
|---|---|---|
| 5,524,620 A | 6/1996 | Rosenschein |
| 5,582,176 A | 12/1996 | Swerling et al. |

(Continued)

OTHER PUBLICATIONS

Bravata, D., et al., Thrombolysis for Acute Stroke in Routine Clinical Practice, Arch Intern Med, vol. 162, pp. 1994–2001, Sep. 23, 2002.

Nishioka, T., et al., Dissolution of Thrombotic Arterial Occlusion by High Intensity, Low Frequency Untrasound and Dodecafluoropentane Emulsion: An In Vitro and In Vivo Study, Journal of the American College of Cardiology, vol. 30, No. 2, pp. 561–568, Aug. 1997.

(Continued)

*Primary Examiner*—Ali Imam
(74) *Attorney, Agent, or Firm*—Ray F. Cox, Jr.

(57) ABSTRACT

An apparatus and method for using ultrasound augmented with microbubbles, thrombolytic drugs or other agents for clot lysis wherein at least one ultrasound transducer generates a plurality of acoustic signals and time, amplitude, phase and frequency modulation of the signals provide more uniform power delivery with fewer gaps in the ultrasound field. Interference patterns from one or multiple transducers are constantly shifted in position. A phased array of transducers may generate a beam that is swept over the area to be treated. In another embodiment, an array of transducers may generate ultrasound at a number of slightly varying frequencies to produce an interference pattern that sweeps in and out through the targeted tissue. A single array may be used to produce both effects simultaneously or separately.

26 Claims, 8 Drawing Sheets

U.S. PATENT DOCUMENTS

| | | | |
|---|---|---|---|
| 5,648,098 | A | 7/1997 | Porter |
| 5,695,460 | A | 12/1997 | Siegel et al. |
| 5,980,950 | A | 11/1999 | Porter |
| 6,113,570 | A | 9/2000 | Siegel et al. |
| 6,126,619 | A | 10/2000 | Peterson et al. |
| 6,139,819 | A | 10/2000 | Unger et al. |
| 6,197,345 | B1 | 3/2001 | Porter |
| 6,416,740 | B1 | 7/2002 | Unger |
| 6,514,220 | B2 | 2/2003 | Melton, Jr. et al. |
| 6,548,047 | B1 | 4/2003 | Unger |
| 6,575,922 | B1 | 6/2003 | Fearnside et al. |
| 6,716,412 | B2 | 4/2004 | Unger |
| 2001/0008880 | A1 | 7/2001 | Porter |
| 2001/0031243 | A1 | 10/2001 | Unger |
| 2002/0082529 | A1 | 6/2002 | Suorsa et al. |
| 2002/0095087 | A1 * | 7/2002 | Mourad et al. ............. 600/442 |
| 2002/0107473 | A1 | 8/2002 | Bond et al. |
| 2002/0193708 | A1 | 12/2002 | Thompson et al. |
| 2004/0059220 | A1 * | 3/2004 | Mourad et al. ............. 600/442 |
| 2005/0015009 | A1 * | 1/2005 | Mourad et al. ............. 600/438 |

OTHER PUBLICATIONS

Tachibana, K., et al., Albumin Microbubble Echo–Contrast Material as an Enhancer for Ultrasound Accelerated Thrombolysis, Circulation, vol. 92, No. 5, pp. 1148–1150, Sep. 1, 1995.

Alexandrov, A., et al., High Rate of Complete Recanalization and Dramatic Clinical Recovery During tPA Infusion When Continuously Monitored with 2–MHz Transcranial Doppler Monitoring, Stroke, vol. 31, pp. 610–614, Mar. 2000.

Schmulling, S., et al., One–Year Follow–Up in Acute Stroke Patients Treated with rtPA in Clinical Routine, Stroke, vol. 31, pp. 1552–1554, Jul. 2000.

Daffertshofer, M., et al., Therapeutic Ultrasound in Ischemic Stroke Treatment: Experimental Evidence, European Journal of Ultrasound, vol. 16, pp. 121–130, Nov. 2002.

Culp, W., et al., Microbubble–augmented Ultrasound Declotting of Thrombosed Arteriovenous Dialysis Grafts in Dogs, J Vasc Interv Radiol, vol. 14, No. 3, pp. 343–347, Mar. 2003.

Culp, W., et al., Microbubble Potentiated Ultrasound as a Method of Declotting Thrombosed Dialysis Grafts: Experimental Study in Dogs, Cardiovascular and Interventional Radiology, vol. 24, pp. 407–412, published online Nov. 8, 2001.

* cited by examiner

ULTRASOUND APPARATUS AND METHOD FOR AUGMENTED CLOT LYSIS

CROSS-REFERENCE TO RELATED APPLICATIONS

This application claims the benefit of U.S. Provisional Application No. 60/501,000 filed Sep. 8, 2003, the disclosure of which is incorporated herein by reference.

STATEMENT REGARDING FEDERALLY SPONSORED RESEARCH OR DEVELOPMENT

Not applicable.

BACKGROUND OF THE INVENTION

The present invention relates to an apparatus and method for using ultrasound augmented with microbubbles, thrombolytic drugs or other lysing agents for clot lysis, and in particular to such an apparatus and method using time, phase and frequency modulation of multiple acoustic signals from one or more ultrasound transducers to provide uniform power delivery with fewer gaps in the ultrasound field.

Thrombosis is the development of a blood clot within a blood vessel. A thrombosis can cause serious, even life threatening, conditions due to partial or total blockage of a blood vessel. Various techniques are known for lysing or removal of the clot. These techniques include the injection of various clot dissolving agents.

Ultrasound has been found to be useful in lysing clots and enhancing the effectiveness of a lysing agent, such as a thrombolytic drug.

More recently, microbubbles have been found to be effective as a lysing agent when used in conjunction with ultrasound. Microbubbles are used in the form of a liquid containing stable microspheres of an insoluble, preferably inert, gas. However, conventional techniques are limited in the size and range of the ultrasound field and suffer from gaps in the field and shadowing caused by differential propagation of the ultrasound field through various shapes, compositions and densities of anatomical structures.

U.S. Pat. No. 6,514,220, the disclosure of which is incorporated herein by reference, discloses that the effect of ultrasound irradiation of a portion of a human or animal body is enhanced by operating a portion of the human or animal body as a trapped mode resonator.

The prior art teaches focusing or concentrating ultrasound energy. However, ultrasound energy focused or concentrated at a single location may produce excessive heating or cavitation, particularly when the acoustic field is static. Static acoustic fields may also suffer from insufficient energy levels or gaps in portions of the field.

BRIEF SUMMARY OF THE INVENTION

The present invention overcomes the problems of the prior art by using one or more ultrasound transducers generating a plurality of acoustic signals at similar or different frequencies to produce traveling interference patterns. Also, the frequency, amplitude and phase from the transducers may be modulated so that any interference pattern will be constantly shifting in position, thereby insuring uniform coverage. In one embodiment, a phased array of transducers may generate a beam that is swept over the area to be treated. In another embodiment, an array of transducers may generate ultrasound at a number of slightly varying frequencies to produce an interference pattern that sweeps in and out through the targeted tissue. A single array may be used to produce both effects simultaneously or separately.

At high power, ultrasound causes physical stresses and a temperature increase within the targeted tissue. The amplitude of the excitation voltage may be manipulated to reduce the heating effect. By using a gating circuit, short bursts of ultrasound may be produced so that the average power delivered to the targeted tissue may be reduced while the intensity of the ultrasound may be kept relatively high during the short ultrasound burst. Further, when microbubbles are employed as the lysing agent, the duration between the ultrasound bursts may be adjusted so as to allow even minimal blood flow to replenish the supply of microbubbles at the surface of the clot that will have been ruptured by the ultrasonic action. As noted above, certain embodiments of the invention may use phased arrays of transducers to move an ultrasound beam around the targeted tissue. Likewise, one or more transducers may generate a plurality of varying frequencies to produce interference patterns of traveling waves of ultrasound that sweep through the targeted tissue. A gating circuit may not be required when either of these embodiments or a combination allow the average power lever to be kept low enough in the targeted tissue to avoid overheating.

Variations in the spatial arrangement of the transducers may be used to change the field shape. The transducers may be moved to continually vary the field. Also, the beam from the ultrasound transducers may be designed in such a way that the beam is dispersed at wide angles, obviating the need for an ultrasound transducer to be aimed directly at a clot. Focusing devices or phased array technology may be used to more widely disperse the beam in a "search light sweep" manner. In one embodiment of the present invention, an array of a large number of transducers would have each transducer excited by a slightly different frequency. The resulting pressure waveform would have periodic large peaks with less average power and the pressure peaks would sweep through the targeted tissue in an in and out manner. Also, by sequenced phasing across the array such that each transducer is driven at the same frequency but differing in phase, this phased array could direct the beam through a wide volume of targeted tissue without moving the transducers. By combining these two embodiments, the resulting maxima and minima of the power deposition moving rapidly through all points in the beam while the beam is sweeping the targeted tissue would result in a much better penetration by this focused beam than by a diffused beam.

BRIEF DESCRIPTION OF THE SEVERAL VIEWS OF THE DRAWING

4A shows a beam too low, FIG. 4B shows a beam too high; and FIG. 4C shows a properly aimed beam. In each case, the basiliar artery is still covered.

FIGS. 7A, 7B and 7C illustrate the coverage of a single transducer, while FIG. 7D illustrates the effect of multiple transducers with overlapping coverage so that no shadowed areas are left without coverage. Also illustrated is the limited range of higher frequency acoustic waves. The effective range in the absence of bone shadowing is shown by the dotted line in each figure. The range as limited by bone shadowing is shown by the solid line in each figure.

DETAILED DESCRIPTION OF THE INVENTION

Known therapeutic ultrasound thrombolysis techniques based on microbubbles, thrombolytic drugs or the like lysing a clot in ultrasound fields are limited in field size and range. Also, ultrasound is absorbed by tissue. Multiple transducers decrease the problems of shadowing and suboptimal energy levels seen with single transducers. The present invention overcomes the limitations of the prior art by using one or more transducers and by frequency, phase and timing modulation of a plurality of acoustic signals to provide more uniform power delivery through traveling waves without the gaps in the fields caused by standing waves. The ultrasound field is manipulated, both temporally and spatially, to maximize both effect and ease of use. Wide application to stroke and problem clots in various applications is expected.

The present invention is unique in that it may be effective in treating ischemic stroke in the human brain where the technique of lysing clots with microbubbles in combination with ultrasound has not been applied. The method and apparatus of the present invention may be used in combination with microbubbles, thrombolytic drugs or other lysing agents.

Figure 5:
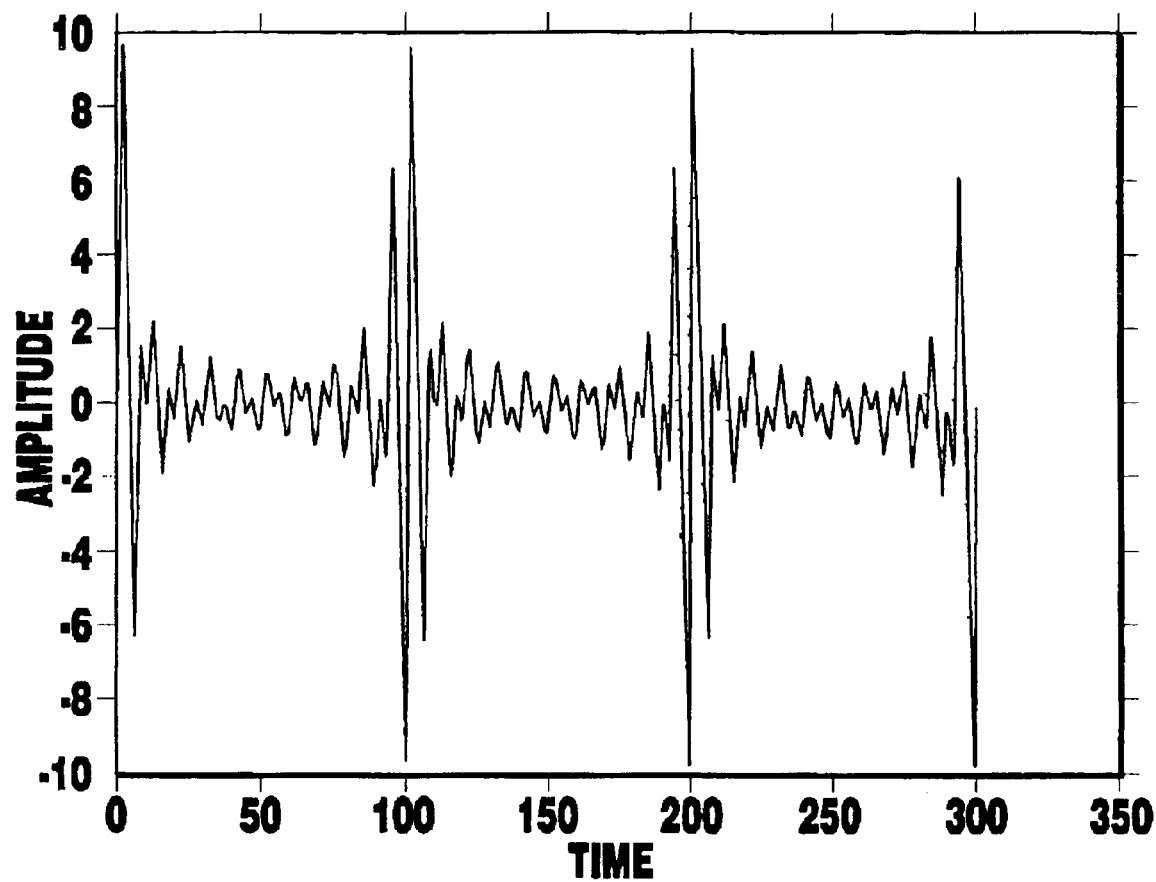
FIG. 5 is a graph showing the predicted pressure wave of ultrasound delivered to a point, where ten ultrasound transducers are each operating at slightly different frequencies.

Interference occurs when two or more ultrasound waves intersect. The waves may be produced directly from an ultrasound transducer or from a reflection from an anatomical structure, such as the surface of the head. Interference may be either constructive or destructive in nature depending upon the relative phase and amplitudes of the combining waves. If the interference is destructive, then when microbubbles are used as the lysing agent, the microbubbles may not expand and contract sufficiently to produce the desired therapeutic effect. The present invention contemplates that the ultrasound frequency and phase from one or more transducers may be modulated so that any interference pattern will be constantly shifting in position, thereby insuring uniform coverage of the targeted anatomical portion of a human or animal body. FIG. 5 shows the predicted pressure wave of ultrasound delivered to a point, where ten ultrasound transducers are operating at slightly different frequencies. The interference pattern of nodes and anti-nodes created thereby is not static but travels through the targeted tissue. The frequencies of the acoustic signals are selected to avoid standing waves from resonance of the anatomical portion into which the acoustics signals are delivered.

In some applications it will be desirable that the ultrasound transducers be designed in such a way that the beam is dispersed at wide angles obviating the need for the ultrasound transducer to be aimed directly at a clot. Precise aiming is less important with the present invention than with older technology. Focusing devices as well as phased array technology allow the beam to be more widely dispersed in a "search light sweep" manner.

Figure 1A:
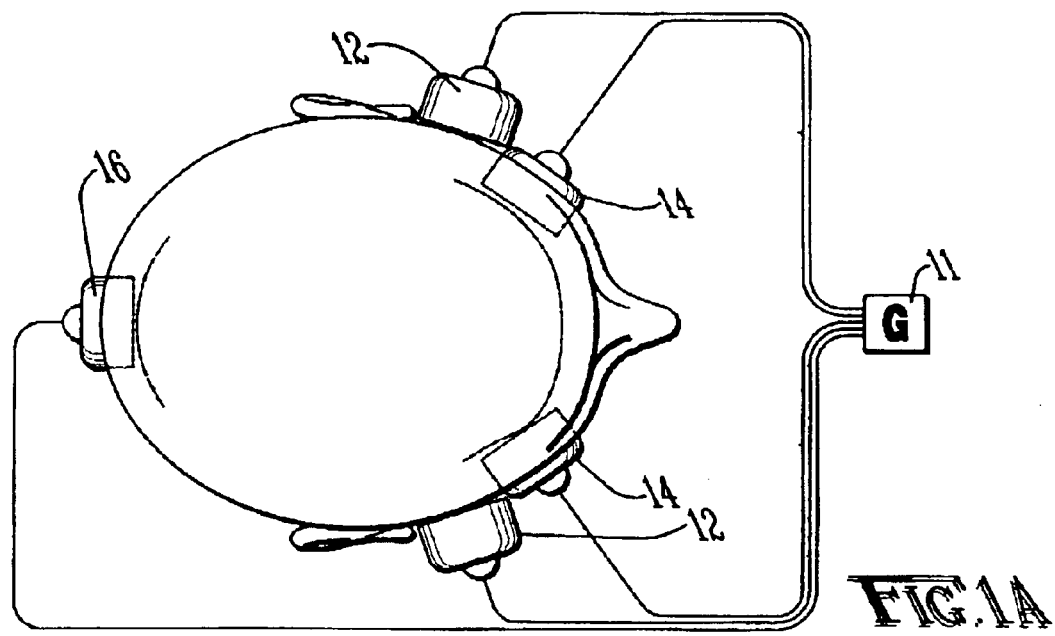
FIG. 1A is a top view of the head of a patient showing a signal generator G feeding multiple transducers.
Figure 1B:
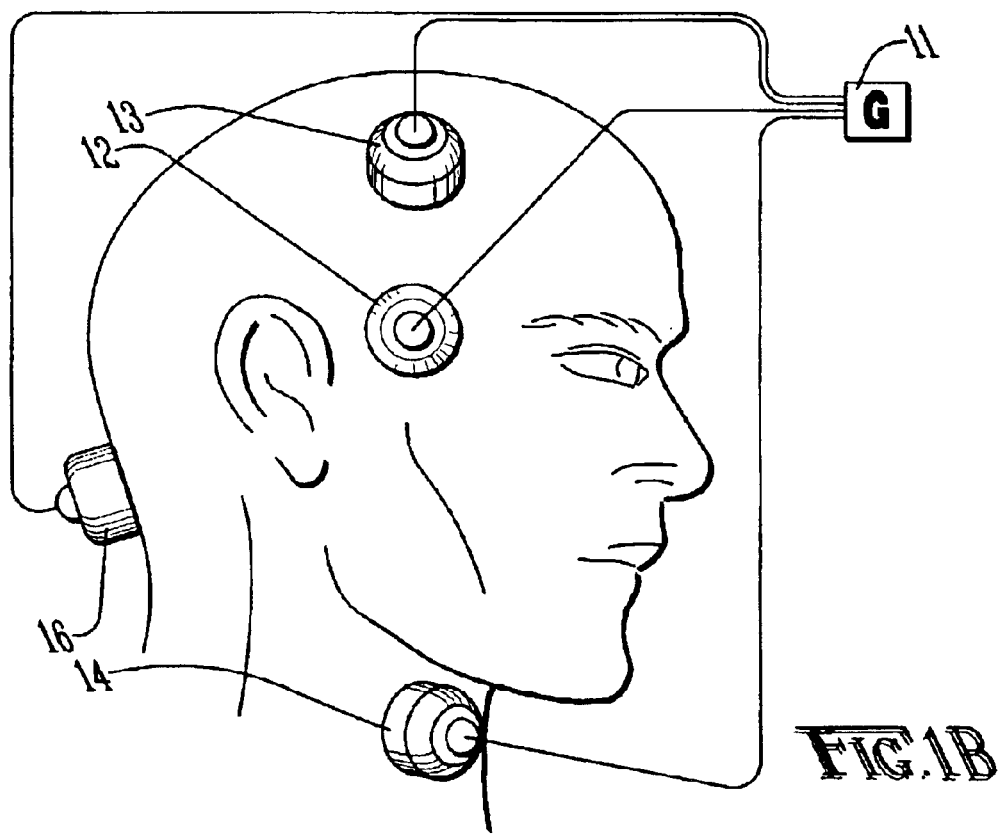
FIG. 1B is a side view of the head of the patient of FIG. 1A.
Figure 1C:
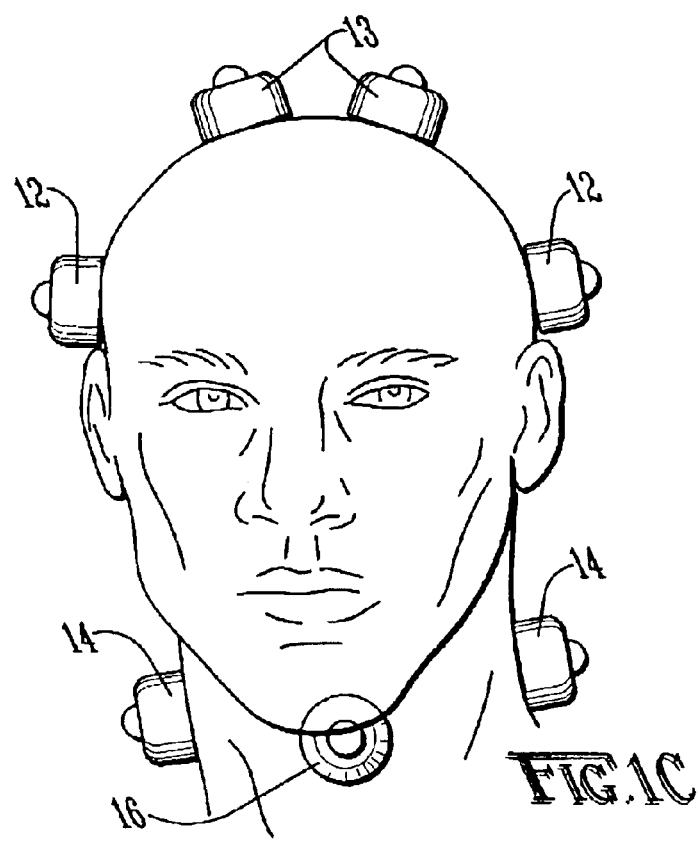
FIG. 1C is a front view of the head of the patient of FIG. 1A.
Figure 2:
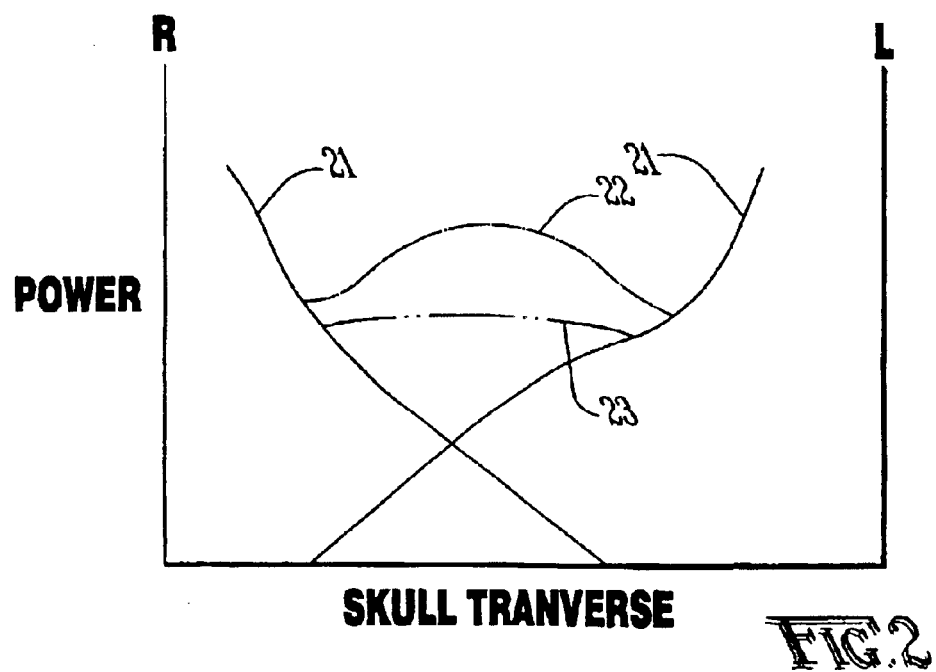
FIG. 2 is a graph of ultrasound power distribution in a cross section of a skull showing how the power distribution varies depending on the number of transducers: one transducer, two transducers or multiple transducers.

Simple variations in transducer arrangement may also be used to change the field shape to match thrombosed arteries, veins, dialysis grafts, and hematomas or collections of thick fluid almost anywhere in the human body. This is illustrated in FIGS. 1A, 1B and 1C, which show a signal generator 11 feeding multiple transducers on the head of a patient, the transducers including temple transducers 12, auxiliary transducers 13 for the skull, neck transducers 14, and posterior neck (suboccipital or occipital) transducers 16. FIG. 2 is a graph of ultrasound power distribution in a cross section of the skull showing how the power distribution varies depending on the number of transducers: one transducer is shown by line 21, two transducers by line 22 or multiple transducers by line 23.

If a node of destructive interference occurs and remains in a single spatial location in the target, then the effectiveness of a microbubble's dispersive action upon a blood clot is suppressed in that location. Likewise, constructive interference could produce detrimental foci of increased power deposition. In the method of the present invention, the amplitude, phase, and nominal excitation frequency may all be changed continuously so that destructive interference, created by a plurality of ultrasonic waves or by reflected waves or by a combination of both, will not allow nodes of destructive interference to remain constantly in one position. If two similar ultrasound transducers are operated at slightly different frequencies and the ultrasonic waves so developed are brought together in a medium, then the interference pattern will move, exchanging nodes and anti-nodes at a frequency that is the difference between the two excitation frequencies. This concept can be expanded to a large number of transducers. The objective of the present invention is to use this well known phenomenon to prevent nodes of destructive interference or constructive interference from holding a constant position. In the case of a reflected wave the original wave interferes with a time delayed version of the same wave. However, in a system as complicated as the human head, the relative phases are quite sensitive to slight changes in the operating frequency of the ultrasonic transducer, especially at higher frequencies. Optimum performance is achieved by simultaneously changing the nominal operating frequency while operating multiple transducers at slightly different frequencies. It is preferable for the frequencies of the acoustic waves to be in a range of 500 kHz and above and more preferably in a range from 500 kHz to 2 MHz. The frequencies are selected so as not to resonate and produce standing waves in the anatomical portion being treated.

In order to obtain a more uniform distribution of energy deposition in a volume, certain characteristics related to high versus low frequency acoustic radiation must be considered. First, low frequency acoustic waves, when directed at a small opening in an anatomical structure, tend to be dispersed since the small opening acts similar to a diverging lens because of diffraction. This effect is not significant at higher frequencies where the wavelength is small relative to the scale of the opening. For example, a beam of 40–100 kHz directed at the foramen magnum in the skull will be significantly dispersed, while a beam of 1 MHz will experience little dispersion when passing through the foramen magnum. Second, acoustic waves are attenuated by bone. This effect is much greater for higher frequencies than for lower frequencies. While higher frequencies may experience 90% losses, a beam of 40 kHz may only see a 60% loss. Third, this attenuation effect is true for tissues other than bone. The significance here is that all acoustic waves will be reflected from structures where the speed of transmission of the acoustic wave changes; e.g., from a less dense medium to a more dense medium as when a wave traveling through soft tissue encounters bone. Since lower frequency waves are attenuated to a lesser extent than higher frequencies, a lower frequency wave may be reflected again and again from anatomical structures before it is attenuated to the point where its contribution to the overall energy field is negligible. Such reflections will interfere constructively and destructively, leading to a buildup in energy levels in the anatomical structure with undesirable peaks in the acoustic energy patterns and standing waves. Higher frequency acoustic waves, in contrast, are more likely to attenuate before multiple reflections can occur. The shorter range of such high frequency waves therefore decreases the uncertainty associated with predicting and controlling the levels of acoustic energy in the anatomical structure. In particular, standing waves may be avoided more easily. The drawback to the use of higher frequencies is the losses due to the higher attenuation compared to lower frequencies. The losses can be overcome by using multiple transducers that are spatially distributed and where the frequency, amplitude and phase of the acoustic signals from each transducer are controlled to produce a more uniform acoustic energy field in the anatomical structure at therapeutically effective levels.

Various frequencies and combinations of frequencies may be desirable in particular circumstances to both avoid standing waves with excessively concentrated energy deposition in particular locations and to provide more uniform distribution of the energy at therapeutic levels. For example, lower frequency acoustic waves, such as 40 kHz, may be better dispersed by refraction of the beam when directed through a small opening in a bone structure, such as the foramen magnum in the skull. The lower frequency provides longer range and better coverage than higher frequencies. In relation to the skull in particular, lower frequencies also pass through bone more efficiently than higher frequencies. In general, acoustic waves at higher frequencies penetrate less well, degrade faster, and are much shorter than lower frequency waves; together these characteristics of higher frequency waves avoid a problem of low frequency waves that may match the scale of anatomical structures and thereby tend to form detrimental large standing waves in such anatomical structures. Also, higher frequencies do not disperse to the same extent as lower frequencies and may therefore be more effective as a straight beam, either aimed at a target or swept through a range of vectors to cover a volume. As discussed above, higher frequencies, above 500 kHz and particularly between 500 kHz and 2 MHz, are helpful in avoiding unanticipated peaks in the energy deposition pattern and standing waves. Combinations of frequencies from spatially dispersed transducers may be employed to effectively treat complex structures. An example would be the combination of a 40 kHz transducer at the back of the skull along with a pair of 1 MHz transducers at the sides of the skull as shown in FIGS. 1A–C and 7A–D. Another example would be a linear array of transducers for treating veins in an extremity.

Figure 6:
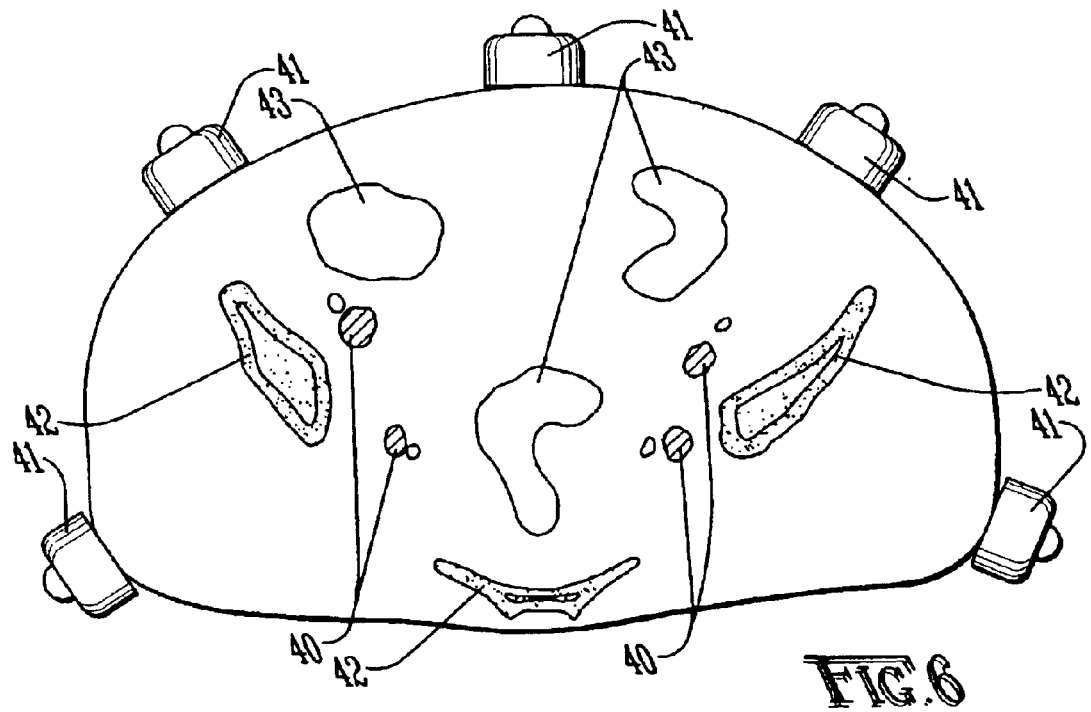
FIG. 6 is an axial view of a human pelvis showing an arrangement of transducers for treating clots in the iliac veins.
Figure 7A:
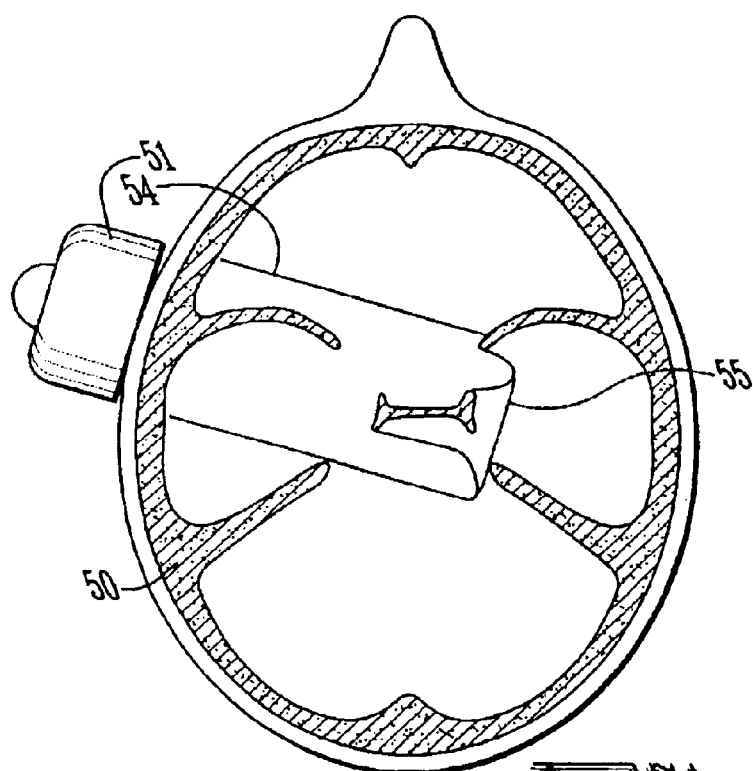
FIGS. 7A, 7B, 7C and 7D are axial views of a human skull showing the effect of bone shadowing on the coverage from each of three transducer locations.
Figure 7B:
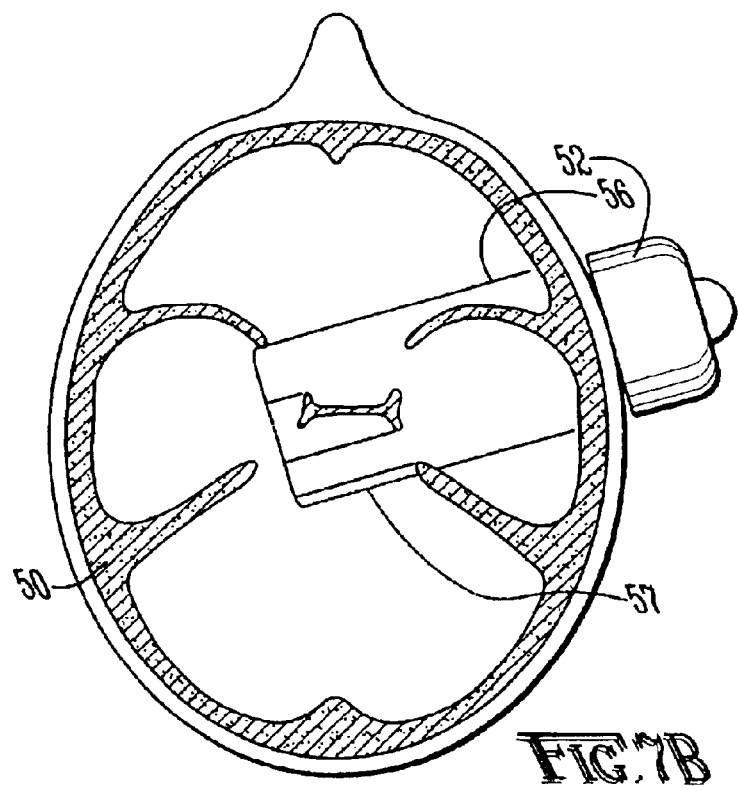
Figure 7C:
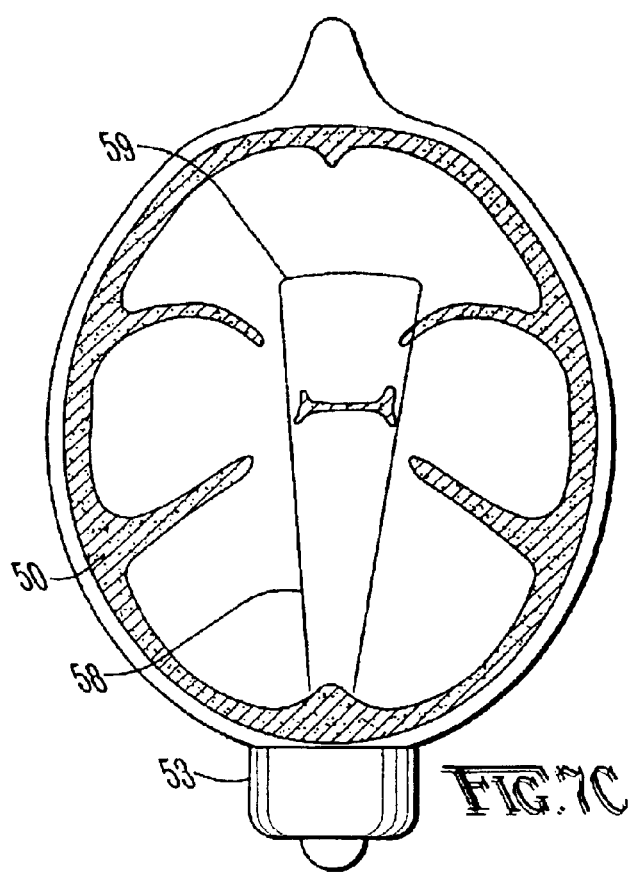
Figure 7D:
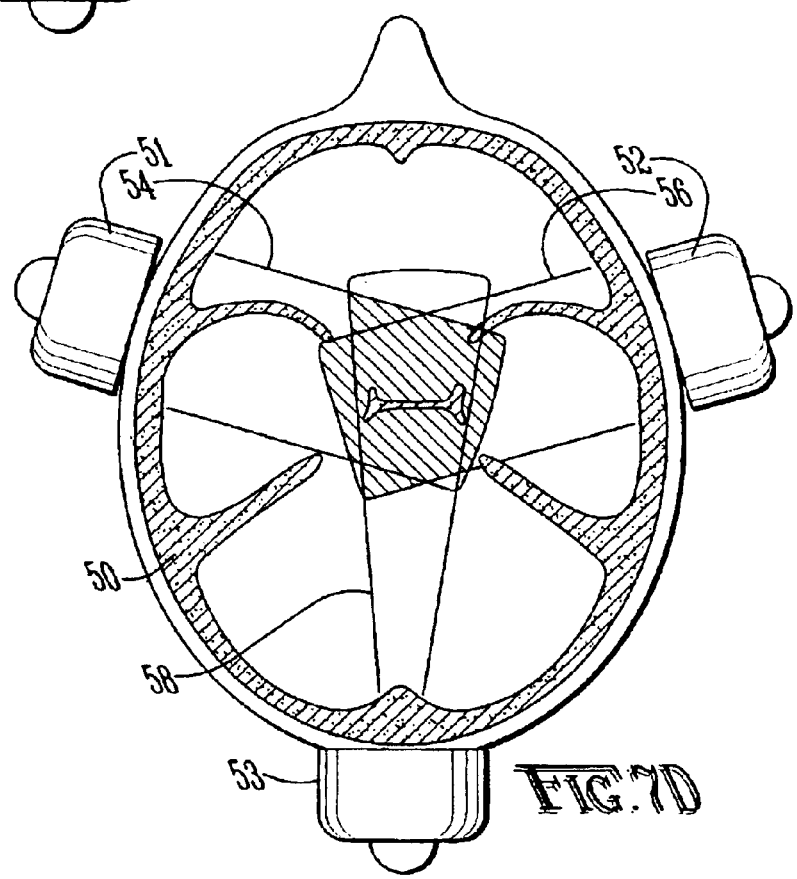

FIG. 6 illustrates an arrangement of transducers suitable for treating clots 40 in the iliac veins. FIG. 6 is an axial view of the human pelvis. Transducers 41 are arranged to avoid shadowing by bone 42 and by bowel 43. The bowel 43 also produces shadowing of the acoustic wave from a transducer 41 due to the presence of air or feces in the bowel 43. FIGS. 7A–D also illustrate an arrangement of transducers to avoid shadowing effects and to produce a more uniform, therapeutically effective acoustic field in a complex anatomical structure. FIGS. 7A–D show an axial view of a human skull 50 with one or more transducers 51, 52, 53 placed in various locations around the skull 50 for treating the anterior, middle and posterior fossas where major vessels supply the brain. In FIG. 7A, transducer 51 is located to cover the right middle cerebral artery and right internal carotid bifurcation. The solid line 54 shows the range of the acoustic wave from transducer 51 where bone shadowing limits the depth of penetration of the acoustic wave. The dotted line 55 shows the range of the acoustic wave in the absence of bone shadowing. Likewise, FIG. 7B shows a transducer 52 located to cover the left middle cerebral artery and left internal carotid bifurcation, where the solid line 56 shows the range as limited by bone shadowing while the dotted line 57 shows the range without bone shadowing. FIG. 7C shows a transducer 53 placed to cover the basilar artery and some branches. The solid line 58 shows the range of the acoustic wave from transducer 53 as limited by shadowing and the dotted line 59 shows the range in the absence of shadowing. FIG. 7D shows the combined effect of transducers 51, 52, 53 to avoid shadowing problems and fill in the gaps low in the intracranial vessels. The overlapping fields of the transducers 51, 52, 53 are shown in FIG. 7D by shading.

Figure 3A:
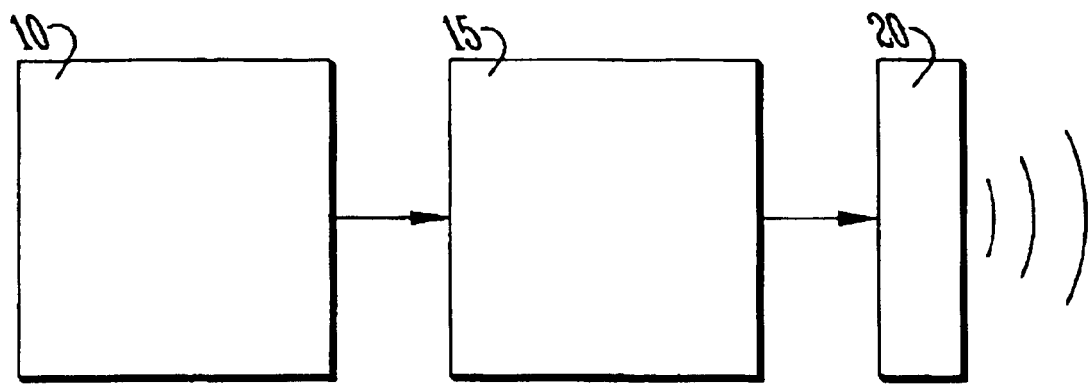
FIG. 3A is a schematic diagram of the apparatus of the present invention.
Figure 3B:
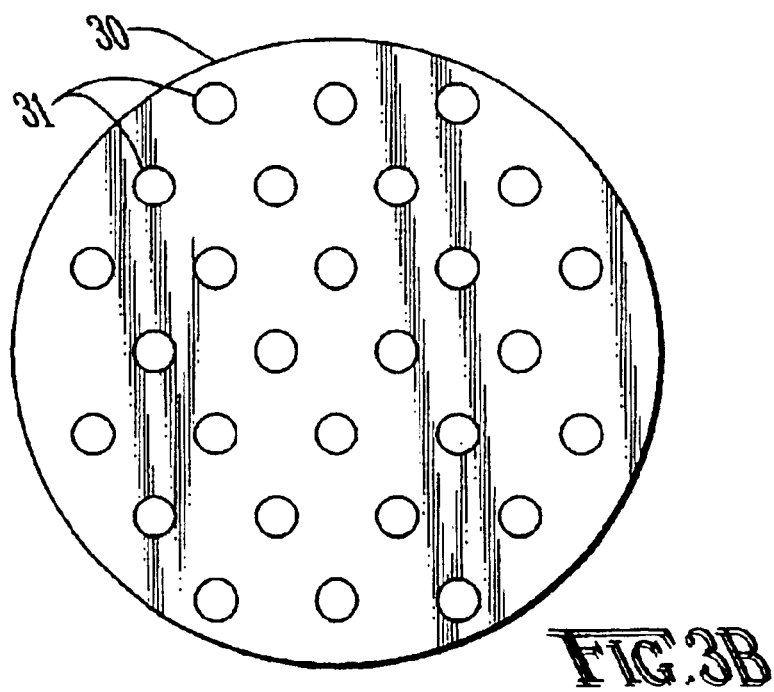
FIG. 3B is an example of an array of ultrasound transducers.

As shown in FIG. 3A, a signal generator 11 may comprise a frequency synthesizer module 10 producing an oscillatory output at a frequency suitable to excite the ultrasonic transducer 20. The oscillatory signal is then amplified by an amplifier and gate 15 to a voltage needed to excite the ultrasonic transducer 20. Finally, the excitation signal may be switched off by the gating circuit of the amplifier and gate 15. The frequency synthesizer 10 and the amplifier and gate 15 are programmable and can be controlled by an eight bit embedded microcontroller (not shown) or other programmable means. Thus the ultrasonic transducer 20 may be excited in a manner so as to force a more uniform coverage of tissue with ultrasound. FIG. 3B is an example of an array 30 of ultrasound transducers 31. By controlling the phase of the ultrasound wave generated by each transducer 31 in the array 30, the pattern of interference between the individual waves as they are propagated outwardly produces a beam which may be directed in any desired pattern to sweep the area being treated. Also, each transducer may be excited at a slightly different frequency to produce an interference pattern where the pressure peaks sweep in and out along the beam. The two embodiments may be combined to produce a beam that sweeps through the targeted tissue while the pressure peaks sweep along the beam. Instead of multiple transducers, a single transducer may be used with a signal generator generating a plurality of acoustic signals having different frequencies, phases and amplitudes. A signal generator may also be used to generate a plurality of acoustic signals having randomly generated frequencies, phases and amplitudes. The signal generator may also use a white noise source to generate the acoustics signals.

Ultrasound is absorbed by tissue and at high power causes a temperature increase within the tissue. The amplitude of the excitation voltage may be manipulated to reduce the heating effect. By using the gating circuit of the amplifier and gate 15, short bursts of ultrasound may be produced so that the average power delivered to the targeted tissue may be reduced while the intensity of the ultrasound may be kept relatively high during the short ultrasound burst. It is known that ultrasound will rupture and destroy microbubbles in the process of clot lysis. This requires repeated delivery of microbubbles for continued lytic effect. The duration between the ultrasound bursts may be adjusted so as to allow even minimal blood flow to replenish the supply of microbubbles at the surface of the clot that will have been ruptured by the ultrasonic action. Also, as noted above, certain embodiments of the invention may use phased arrays of transducers to move an ultrasound beam around the targeted tissue. Likewise, an array employing varying frequencies to produce interference patterns of traveling waves of ultrasound that move through the targeted tissue. The patterns of ultrasound generated by these embodiments may also be used to allowed repeated delivery and replenishment of microbubbles.

Many ultrasonic transducers emit ultrasound into a focused columnar beam. In such a design, the transducer would have to be directed at the location of the clot, which in turn could have to first be located by other means. The present invention would use dispersive elements when the location of the clot was unknown. However, it is not intended to exclude from the scope of the present invention the use of transducers that emit ultrasound into a columnar beam if the location of the clot is known. Furthermore, in certain embodiments of the present invention, a phased array of transducers may be employed to produce a beam that can be aimed by appropriate selection of the respective phases of the acoustic signals. Such a beam may be employed to sweep the area to be treated or can be directed to the location of a clot.

Figure 4A:
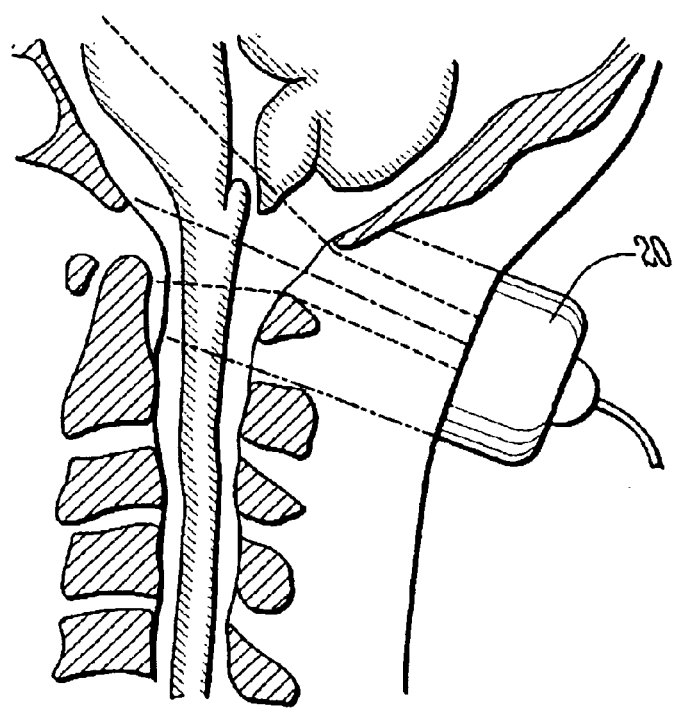
FIGS. 4A, 4B, and 4C are cross sections through the spine and base of the skull illustrating how diffusion of the ultrasound beam makes precise aiming unnecessary. FIG.
Figure 4B:
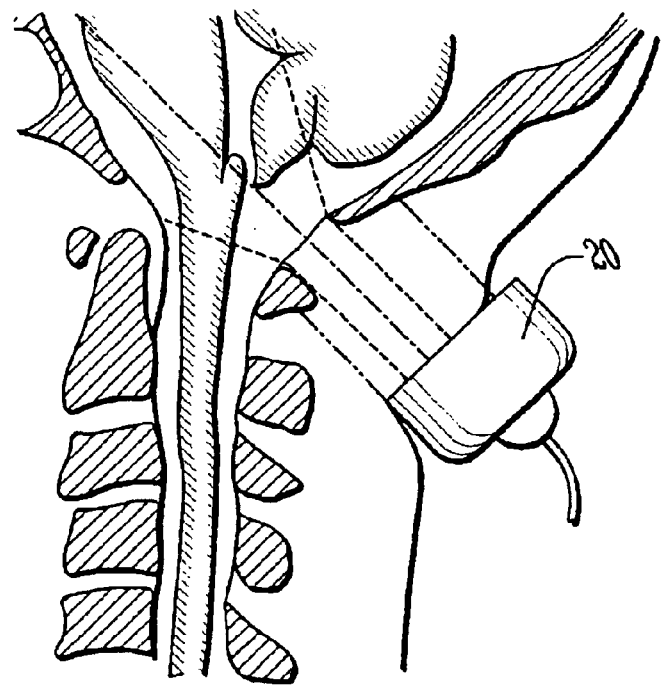
Figure 4C:
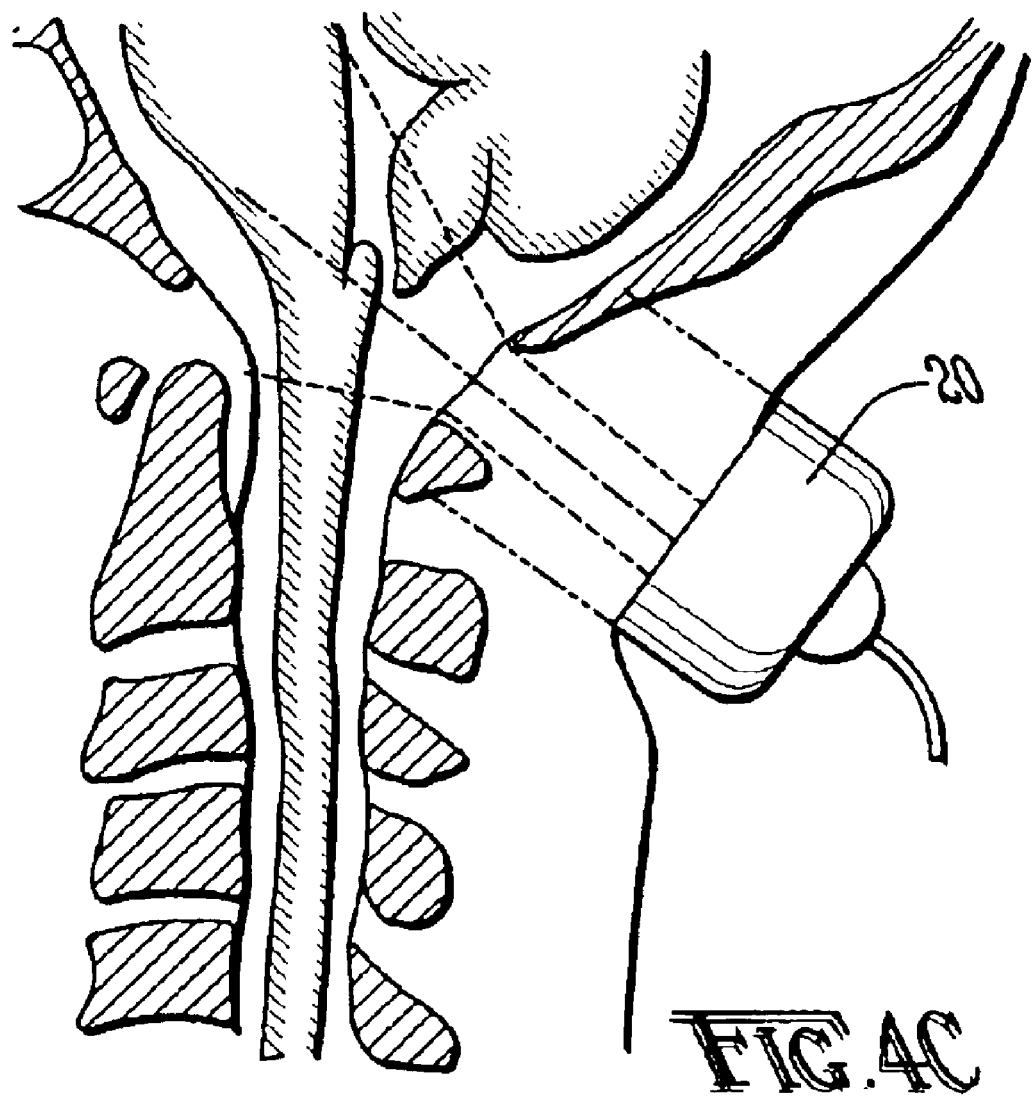

Data using a human skull in a water bath and hydrophone mapping show ultrasound delivery through the foramen magnum using 20 to 80 KHz performs very well (30% of foramen magnum levels) all the way to a point 1 cm above the anterior clinoids. It is still present at the anterior margin of the anterior fossa (18 to 20 cm range) at reduced levels. At the anterior clinoids' 12 to 14 cm range the power levels are nearly equivalent to levels at 5 to 7 cm range through the temporal approach. Shadowing occurs along the inferior aspects of the anterior fossa, which are well filled in by temporal transducers. The shadows posterior to the petrus pyramids when using the temporal approach are well filled in by the foramen magnum transducer. Good diffusing of the beam through the foramen along with good reflections from various structures fill much more of the skull than a linear beam would suggest. Ultrasound diffusion makes aiming the beam unnecessary. With reference to FIGS. 4A, 4B and 4C, it is shown that a beam too low (FIG. 4A), too high (FIG. 4B), or properly aimed (FIG. 4C) still covers the basiliar artery.

Moreover, we have experimentally shown that by changing the frequency about 10% up or down from the primary frequency of 40 KHz, the nodes and anodes are swept completely across every particular point in the beam. This is about half of the change we anticipated and is probably due to the multiple harmonics our current transducers produce. This completely covers the targeted tissue and negates the problem of shadowed areas produced by the longer wavelength that is required to get the diffusing refraction of the beam through the foramen magnum.

Frequency agile and interval agile combinations of pulsed wave (each transducer firing in 2 to 20% of the time cycle) ultrasound can be sequenced to avoid mutual interference and completely fill the skull with therapeutic levels of the ultrasound required to lyse a clot with microbubbles, thrombolytic drugs or other lysing agents.

The entire basilar artery and upper portions of the vertebral arteries can now be added to the coverage of the internal carotids, middle cerebrals, anterior cerebrals, and Circle of Willis previously covered with 1 MHz temporal transducers. This is important due to the high mortality of basilar artery strokes and the absence of any good therapy for them.

What is claimed is:

1. An apparatus for generating acoustic fields in an anatomical portion of a human or animal body, comprising:
    at least one acoustic transducer for injecting a plurality of acoustic signals into the anatomical portion, and
    a signal generator generating said plurality of acoustic signals, said plurality of acoustic signals being characterized by respective frequencies, phases and amplitudes defining acoustic pressure peaks that continually vary temporally and spatially throughout said anatomical portion to avoid continuous standing waves in said anatomical portion.

2. The apparatus of claim 1 wherein said plurality of acoustic signals are characterized by respective frequencies, phases and amplitudes selectable to generate interference patterns among said plurality of acoustic signals, wherein said interference patterns define acoustic pressure peaks that continually vary temporally and spatially throughout said anatomical portion to avoid continuous standing waves in said anatomical portion.

3. The apparatus of claim 1 wherein said respective frequencies are selectable to avoid resonance of said plurality of acoustic signals in said anatomical portion.

4. The apparatus of claim 1 wherein a plurality of transducers are spatially distributed about said anatomical portion.

5. The apparatus of claim 1, wherein said signal generator comprises means for selecting said respective frequencies from a range of 500 kHz and above.

6. The apparatus of claim 5, wherein said signal generator comprises means for selecting said respective frequencies from a range of 500 kHz to 2 MHz.

7. The apparatus of claim 1, wherein said signal generator comprises means for randomly generating said respective frequencies, phases and amplitudes of said plurality of acoustic signals.

8. The apparatus of claim 1, wherein said signal generator comprises means for generating said plurality of acoustic signals from a white noise generator.

9. The apparatus of claim 1, wherein said signal generator further comprises means for sweeping said respective frequencies over a range of frequencies.

10. The apparatus of claim 1, further comprising an array of transducers and wherein said signal generator comprises means for controlling said respective phases of said plurality of acoustic signals whereby said plurality of acoustics signals form a directed beam.

11. A method for generating acoustic fields in an anatomical portion of a human or animal body, comprising the steps of:
    providing at least one acoustic transducer for injecting a plurality of acoustic signals into the anatomical portion, and
    providing a signal generator generating said plurality of acoustic signals, said plurality of acoustic signals being characterized by respective frequencies, phases and amplitudes defining acoustic pressure peaks that continually vary temporally and spatially throughout said anatomical portion to avoid continuous standing waves in said anatomical portion.

12. The method of claim 11 wherein said plurality of acoustic signals are characterized by respective frequencies, phases and amplitudes selectable to generate interference patterns among said plurality of acoustic signals, wherein said interference patterns define acoustic pressure peaks that continually vary temporally and spatially throughout said anatomical portion to avoid continuous standing waves in said anatomical portion.

13. The method of claim 11 wherein said respective frequencies are selectable to avoid resonance of said plurality of acoustic signals in said anatomical portion.

14. The method of claim 11 wherein a plurality of transducers are spatially distributed about said anatomical portion.

15. The method of claim 11, wherein said signal generator comprises means for selecting said respective frequencies from a range of 500 kHz and above.

16. The method of claim 15, wherein said signal generator comprises means for selecting said respective frequencies from a range of 500 kHz to 2 MHz.

17. The method of claim 11, wherein said signal generator comprises means for randomly generating said respective frequencies, phases and amplitudes of said plurality of acoustic signals.

18. The method of claim 11, wherein said signal generator comprises means for generating said plurality of acoustic signals from a white noise generator.

19. The method of claim 11, wherein said signal generator further comprises means for sweeping said respective frequencies over a range of frequencies.

20. The method of claim 11, further comprising an array of transducers and wherein said signal generator comprises means for controlling said respective phases of said acoustic signals whereby said acoustics signals form a directed beam.

21. The method of claim 20 wherein said directed beam is swept across an area of said anatomical portion.

22. The method of claim 20 wherein said directed beam is directed to a particular location within said anatomical portion.

23. The method of claim 11, further comprising the step of introducing at least one lysing agent to said anatomical portion.

24. The method of claim 23 wherein said lysing agent comprises microbubbles.

25. The method of claim 23 wherein said lysing agent comprises a thrombolytic drug.

26. The method of claim 23 wherein said lysing agent comprises a combination of microbubbles and a thrombolytic drug.

* * * * *